(12) United States Patent
Russo

(10) Patent No.: US 11,508,459 B2
(45) Date of Patent: Nov. 22, 2022

(54) MODIFIED FBA IN A PRODUCTION NETWORK

(71) Applicant: X Development LLC, Mountain View, CA (US)

(72) Inventor: Frank Russo, Sunnyvale, CA (US)

(73) Assignee: X Development LLC, Mountain View, CA (US)

( * ) Notice: Subject to any disclaimer, the term of this patent is extended or adjusted under 35 U.S.C. 154(b) by 1302 days.

(21) Appl. No.: 15/885,463

(22) Filed: Jan. 31, 2018

(65) Prior Publication Data

US 2019/0236243 A1 Aug. 1, 2019

(51) Int. Cl.
*G16B 5/00* (2019.01)
*G06F 17/16* (2006.01)
*G06F 111/10* (2020.01)

(52) U.S. Cl.
CPC .............. *G16B 5/00* (2019.02); *G06F 17/16* (2013.01); *G06F 2111/10* (2020.01)

(58) Field of Classification Search
None
See application file for complete search history.

(56) References Cited

U.S. PATENT DOCUMENTS

2017/0140092 A1* 5/2017 Palsson ................ G16B 20/00

FOREIGN PATENT DOCUMENTS

WO 02/055995 A2 7/2002
WO WO 2014/015196 A2 1/2014

OTHER PUBLICATIONS

Oberhardt et al. Methods in Molecular Biology, Systems Biology; vol. 500:61-80 (Year: 2009).*
Karr et al. Cell; vol. 150:389-401 (Year: 2012).*
International Report on Patentability dated Aug. 13, 2020 in related application No. PCT/US2018/065139, all pgs.
Brandes et al., "Inferring Carbon Sources From Gene Expression Profiles Using Metabolic Flux Models", Plos One, vol. 7, Issue 5, May 2012, pp. 1-12.
Metris et al., "Modelling Osmotic Stress by Flux Balance Analysis at the Genomic Scale", International Journal of Food Microbiology, vol. 152, No. 3, 2012, pp. 123-128.
PCT/US2018/065139, "International Search Report and Written Opinion", dated Jun. 14, 2019, 14 pages.
Raman et al., "Flux Balance Analysis of Biological Systems: Applications and Challenges", Briefings in Bioinformatics, vol. 10, No. 4, Mar. 15, 2009, pp. 435-449.

* cited by examiner

*Primary Examiner* — Lori A. Clow
(74) *Attorney, Agent, or Firm* — Kilpatrick Townsend & Stockton LLP

(57) ABSTRACT

A method for matching production of FBA metabolism to supply and demand within a larger production network is described herein. An objective function of FBA metabolism is modified to include an upstream supply generated in upstream sub-units, as well as a downstream demand generated within downstream sub-units in the production network. FBA metabolism and the upstream and downstream sub-units are iteratively solved with updated initial conditions, producing a time series solution to the production network.

22 Claims, 6 Drawing Sheets

MODIFIED FBA IN A PRODUCTION NETWORK

BACKGROUND

Field of Art

This description generally relates to matching a rate of production of a set of inputs to a downstream rate of demand, and in particular to modifying an objective function of a flux balance analysis representation of the production network.

Description of the Related Art

A cell's metabolism can be represented as a set of linked reaction pathways between molecules, in which the stoichiometric coefficients of reactions function as constraints on the metabolic system's ability to generate the products of metabolism. The stoichiometric coefficients can be used as constraints in a flux balance analysis (FBA) representation of metabolism. FBA is solved for a steady state behavior of the metabolic system, producing a set of input and output fluxes at the boundaries of the metabolic system. The input flux values represent rates at which metabolism takes in reactants, while the output flux values represent rates at which metabolism supplies products.

Under conventional "pure" FBA, one assumes that the behavior modeled by FBA is a closed system, such that production and consumption of every molecule is internal to the metabolic network. Thus in conventional FBA, production matches consumption exactly, leading to a strict mass balance requirement between molecule input and output fluxes. However, pure FBA metabolism does not contain obvious control points from which to adjust production to any actual demand outside of FBA. This problem is compounded by the fact that pure FBA is time independent, such that the flux values are solved for in a single, one-time calculation, preventing time-dependent adjustment of pure FBA production to meet external demand. Conventional solutions to adjusting FBA include artificially limiting the inputs of metabolism, however this does not provide a way to match the metabolic rate to the actual demand within the cell, as reflected in the multiple sub units of the whole cell model.

SUMMARY

A production network integrates FBA metabolism with a plurality of sub-units, each of which contains its own production and consumption of molecules. Sub-units represent biological processes external to metabolism. The production of molecules within FBA metabolism is regulated by the production of inputs to metabolism within upstream sub-units, as well as the consumption of the outputs of metabolism within downstream sub-units of the production network. An objective function of FBA metabolism is modified to reflect upstream supply, downstream demand, and the existing molecule concentrations within the production network. A time series solution of the production network iteratively solves FBA metabolism with new initial conditions produced at each time step.

A method for simulating an outcome of a cell process includes receiving an initial state dataset based on initial net demand for a plurality of molecules in a plurality of sub-units representing production and consumption of molecules external to an FBA system. The method includes calculating an initial solution flux dataset by evaluating the FBA system based on a stoichiometric matrix and an objective function limited by the initial state dataset. The method includes receiving a subsequent net demand for the plurality of molecules from initial solutions to the plurality of sub-units. A subsequent state dataset is calculated based on the initial state dataset, the initial solution flux dataset and the subsequent net demand. A subsequent solution flux dataset is calculated by evaluating the FBA system with an updated objective function limited by the subsequent state dataset. An outcome of the cell process is determined, including calculating a difference between the subsequent solution flux dataset and the initial solution flux dataset.

DETAILED DESCRIPTION OF DRAWINGS

I. Context

Figure 1:
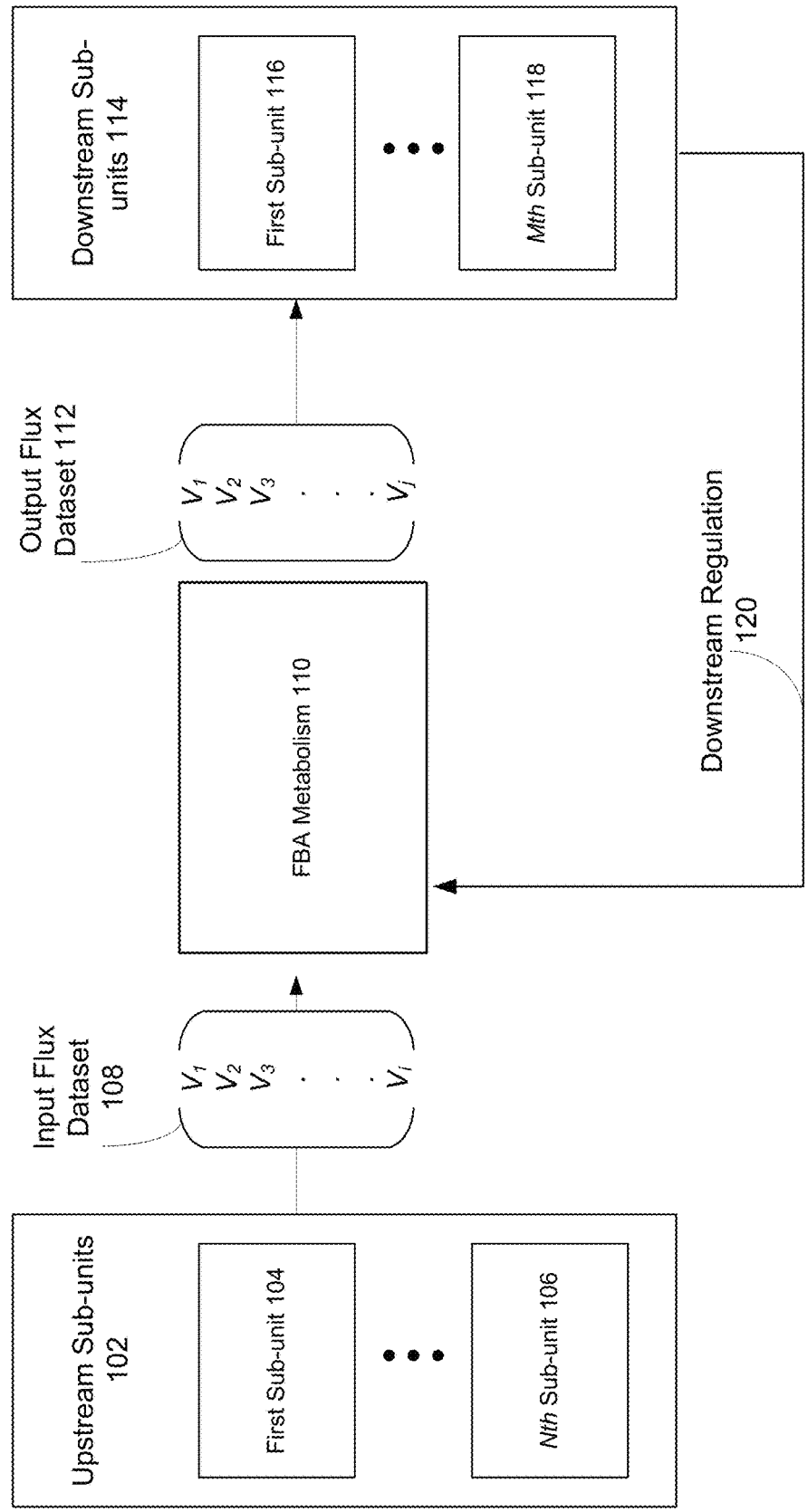
FIG. 1 is a block diagram illustrating a modified FBA system, according to one embodiment.

To formulate the behavior of a metabolic system as an optimization problem, a metabolic system can be represented as a set of linked reaction pathways between molecules, in which the stoichiometric coefficients of reactions function as constraints on the metabolic system's ability to generate the products of metabolism. These stoichiometric constraints are fixed by elemental and charge balance, and are fully time independent. The resulting set of equations for steady state behavior are also time independent. In a "pure" FBA model, in which it is assumed that production and consumption are contained within the closed system of the metabolic network, a set of mass balance equations can be written such that production matches consumption exactly. These linear equations represent a strict mass balance requirement between the input and output fluxes of molecules. An objective function is formed by summing a proportional contribution of each molecule to the reaction network (i.e. the input and output flux values). Biologically, the objective function represents the total biomass of the system. By assuming that a cell will maximize growth (i.e. maximize the total biomass) one can solve for the flux values by maximizing the single value of the objective function given stoichiometric reaction constraints. This leads to exact solutions to all of the flux values of molecules into and out of the metabolic system. Because in pure FBA production and consumption of metabolites do not exist outside of the FBA model, the use of an objection function formed only by the input and output flux values is sound. Within the closed FBA system, the objective function is an exhaustive descriptive of the forces (supply and demand fluxes) governing the system.

Flux Balance Analysis (FBA) is a powerful tool for modeling metabolic systems, since FBA allows for the steady state behavior of the system to be solved without knowledge of intermediate, dynamic behavior, and in part as a result is computationally cheaper than time-dependent dynamic models. These factors make FBA an attractive way of formulating the behavior of metabolism.

However, not all cellular processes have behavior conducive to an FBA formulation, and to build a simulation of a whole-cell model, FBA metabolism interacts with other sub-units which may have their own production and consumption of some of the same molecules within the FBA network. These sub-units simulate processes external to metabolism and contribute to the whole-cell model. The whole-cell model can be conceptualized as a production network, wherein molecules are produced, consumed, and transferred between multiple sub-units in an interconnected network of supply and demand. The externalization of supply and demand to these other sub-units outside of the FBA system breaks the closed-system, mass balance assumption of pure FBA. Pure FBA does not contain obvious control points from which to adjust the production rate of metabolites (i.e. the flux values) to actual demand outside of FBA as reflected by consumption of metabolites in the other sub-units. This problem is compounded by the fact that pure FBA is time independent, such that the flux value solutions are solved for in a single, one-time calculation, preventing time-dependent adjustment of pure FBA to meet external demand. Conventional solutions to adjusting FBA include artificially limiting the inputs of metabolism, however this does not provide a way to have the metabolic rate match actual demand within the production network of a cell.

In order to integrate FBA into the larger production network, the present description modifies the FBA objective function to provide a set of assumptions and controls that more accurately reflect dynamic changes in supply and demand, allowing for use of FBA to simplify computation of the production network without sacrificing fidelity to actual balanced regulation of production and consumption within the network. Specifically, adjusting the optimization target from maximum production or growth (e.g., maximizing output flux values) to regulated growth given the supply and demand within other sub-units represents a shift from a "maximize production" to a "lean-manufacturing" framework of the movement of molecules through the production network.

Thus one primary assumption of FBA that is modified is that of maximum growth or production, represented by maximizing the "biomass" objective function. In pure FBA, maximizing the objective function translates to the idea that all available reactants are converted into the maximum amount of products possible. This also means that the only production constraints other than the fixed stoichiometric constrains are the input flux values or availability of products. However, in reality, FBA metabolism is regulated not only by the amount of reactants available, but also by how much of a given product is consumed by other biological processes, or is already present elsewhere in the production network. Additionally, at some point, production and cellular growth rates are limited not by the supply of inputs, but by the limitations inherent in biological processes, such as the maximum rate of RNA elongation, polypeptide elongation, cell wall assembly, etc. that will limit a cell's growth and impose constraints on the production network. Thus pure FBA intrinsically only allows for upstream control of production, whereas the cell engages in both upstream and downstream control and also has inherent limits on a cell's growth rate.

By modifying the objective function, the production of FBA can be matched to meet actual demand, represented by the rates of production and consumption of metabolites in other sub-units, as well as the concentration of metabolites in reserve in the cell. Furthermore, the objective function can be iteratively updated with new initial conditions following each time step of the time-dependent external sub-units to recast FBA as a dynamically responsive formulation of metabolism. Modifications to the objective function can be verified to determine if the resulting exchange fluxes and the inferred cell growth rate are biologically sound by comparing to real life cellular behavior.

II. FBA Metabolism Within System of Sub-Units

FIG. 1 is a block diagram illustrating a modified FBA system 100, according to one embodiment. Within the modified FBA system 100, an FBA metabolism 110 interfaces with upstream sub-units 102 and downstream sub-units 114. Within the upstream sub-units 102, there may be any number of individual sub-units, such as first sub-unit 104 through Nth sub-unit 106, where N is the total number of upstream sub-units. Within the downstream sub-units 114, there are also any number of individual sub-units, such as first sub-unit 116 through Mth sub-unit 118, where M is the total number of downstream sub-units. The rate of production of FBA metabolism 110 is given by the output flux dataset 112. The rate of supply of raw inputs to metabolism is given by the input flux dataset 108. Upstream sub-units 102 produce the raw inputs to metabolism, such that the rate at which raw inputs are delivered to the FBA metabolism 110 is determined in part by production rates within the upstream sub-units 102. Downstream sub-units 114 consume the products of metabolism, and adjust the production within FBA metabolism 110 through downstream regulation 120. The FBA system 100 is thus an interconnected system of supply and demand, in which FBA metabolism is regulated to produce molecules at a rate limited in part by the upstream sub-units 102 and driven in part by the downstream sub-unites 114.

A. Sub-Units

The upstream and downstream sub-units (102 and 114, respectively) as shown in the modified FBA system 100 represent biological processes external to metabolism. For example, upstream and downstream sub-units 102 and 114 may represent transcription, translation, cellular communication, cellular reproduction, cellular transport, etc. Each of these sub-units encloses its own reaction network, which converts input molecules for the particular biological process represented by the sub-unit to output molecules that are products of the cellular process. Thus each sub-unit contains its own system of production and consumption of molecules.

In upstream sub-units 102, the products of each of the individual sub-units (first sub-unit 104 through Nth sub-unit 106) are used as the raw inputs to FBA metabolism 110. For example, if first sub-unit 104 represents translation, it may take in as inputs mRNA and rRNA, and output various polypeptides. These polypeptides may then be inputs of metabolism and have an input flux value in the input flux dataset 108. Thus the molecules which have input flux values in the input flux dataset 108 may be products of the cellular processes represented by upstream sub-units 102.

Similarly, in downstream sub-units 114, the products of FBA metabolism 110 which have output flux values in the output flux dataset 112 are used as the raw inputs to the downstream cellular processes represented by the individual downstream sub-units. For example, if FBA metabolism 110 produces ATP, this may be used as an input to cell transport as represented by first sub-unit 116. Thus ATP has an output flux value in the output flux dataset 112 that is delivered to the first sub-unit 116.

In some examples, upstream sub-units 102 and/or downstream sub-units 114 may contain molecules that are both inputs to FBA metabolism 110 and that use the products of FBA metabolism 110 as raw inputs. In these examples, a sub-unit may be classified as both an upstream sub-unit 102 and a downstream sub-unit 114. For example, a sub-unit modeling translation may consume amino acids that are produced by FBA metabolism 110 (e.g., the sub-unit is a downstream sub-unit 114), and generate polypeptides that are used as inputs to FBA metabolism 110 (e.g., the sub-unit is also an upstream sub-unit 114).

A sub-unit's designation as an upstream sub-unit 102 and/or a downstream sub-unit 114 is not a static designation, and may change during a simulation of the FBA system 100 in response to changes in supply and demand within the FBA system 100. For example, if there is a demand within first sub-unit 116 for the output of FBA metabolism 110, the first sub-unit 116 may be considered one of the downstream sub-units 114. However, if the demand decreases and the product of first sub-unit 116 builds up in excess, the first sub-unit 116 may become one of the upstream sub-units 102 and its excess product input to and broken down by FBA metabolism 110.

The sub-units in the upstream sub-units 102 and downstream sub-units 114 are mathematical models of the cellular processes they represent. These mathematical models simulate the system of production and consumption of molecules within each sub-unit. Upstream sub-units 102 and downstream sub-units 114 may be Monte Carlo models, modeled with a system of partial differential equations (PDEs), a system of ordinary differential equations (ODEs), FBA, rate kinetics, numerical approximations, or any other mathematical formulation capable of describing the behavior of cellular processes or multivariable systems. At least one sub-unit in the upstream sub-units 102 and downstream sub-units 114 may be time-dependent. While each sub-unit may have a unique mathematical formulation, each sub-unit bounds a set of molecules which are inputs, products or intermediates in the set of reactions and processes modeled by the sub-unit. Each sub-unit implicitly (as in PDE, ODE and Monte Carlo models) or explicitly (as in FBA or rate kinetic models) contains a set of rates at which the sub-unit intakes raw inputs and outputs products. In some examples, an implicit rate of demand may be determined by a difference between an existing concentration of a molecule and a projected concentration in a future time step. For the purposes of the modified FBA system 100, the behavior of the upstream sub-units 102 and downstream sub-units 114 that is relevant to FBA metabolism 110 is the conversion rate of reactants to products within each of the sub-units, since this is the primary value translatable into the terms governing FBA (e.g., the flux values). For each sub-unit, the intake rate of inputs represents the demand for each of the input molecules, while the output rate of products represents the supply of each of the output molecules. As discussed above, molecules are common to the systems of upstream sub-units 102, the FBA metabolism 110 and downstream sub-units 114. For example, ATP may be used in all of the upstream sub-units 102, FBA metabolism 110 and all of the downstream sub-units 114. In aggregate, the outputs of all of the upstream sub-units represent a supply rate of the input molecules of FBA metabolism 110. Thus the output rate of products for the upstream sub-units 102 in part define the input flux values of the input flux dataset 108.

Similarly, in aggregate, the rate at which downstream sub-units 114 take in the output products of FBA metabolism 110 gives a downstream rate of demand for the products of FBA metabolism 110. To adjust the rate of production of FBA metabolism 110, downstream regulation 120 feeds back into the FBA metabolism 110 by modifying the objective function of FBA metabolism 110. This process is described in further detail with reference to FIG. 3.

In addition to upstream supply and downstream demand, the FBA metabolism 110 may be adjusted based on existing concentrations of molecules within the cell. For example, within the reaction networks of upstream sub-units 102, there may be existing concentrations of molecules available to the reaction networks within each sub-unit. These existing concentrations will affect supply and demand, since reaction rates are concentration dependent, and thus accumulation of a product will lead to a decrease in the rate at which molecules move through a reaction pathway. Conversely, a low concentration of a molecule may lead to an increase in flux rates through a reaction pathway. Existing concentration of molecules may be calculated within the upstream sub-units 102 and downstream sub-units 114, as well as within representative "storage" of molecules within the cell. This "storage" is described in further detail with reference to FIG. 2.

B. Determining Input and Output Flux Datasets

Thus the FBA metabolism 110 operates within a larger system of supply and demand located within the upstream sub-units 102 and downstream sub-units 114, which ultimately affect both the input flux dataset 108 and output flux dataset 112 containing the flux value solutions to the FBA formulation of the metabolic system. To solve for the input flux dataset 108 and output flux dataset 112, a system of equations describing the stoichiometric reaction constraints for each molecule in the FBA metabolism 110 is defined. The flux values of each molecule (e.g., the input supply of FBA metabolism 110 and the output production of FBA metabolism 110) are unknowns, and are solved for by summing the modified weighted flux values to produce an objective function. The objective function is then maximized given the constraints of the system of equations. Solving the maximization problem produces a set of flux value solutions which make up the input flux dataset 108 and the output flux dataset 112. The flux value solutions of the input flux dataset 108 and output flux dataset 112 represent the steady state behavior of FBA metabolism 110 given the existing supply and demand within upstream sub-units 102 and downstream sub-units 114. This process is described in further detail with reference to FIG. 3.

III. Example Full-Cell Model with Modified FBA Metabolism

Figure 2:
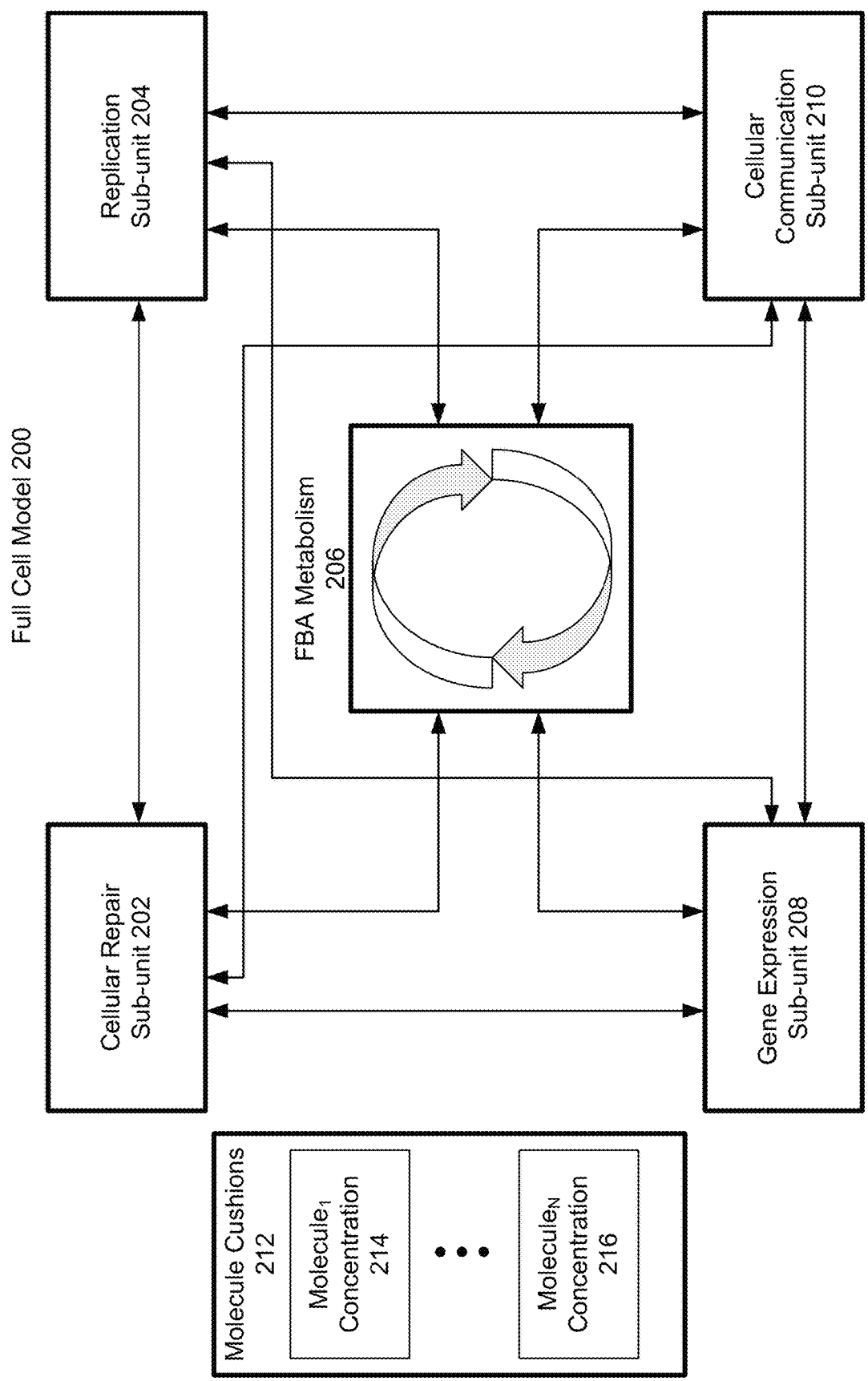
FIG. 2 is a block diagram of a full cell model with modified FBA metabolism, according to one embodiment.

FIG. 2 is a block diagram of a full cell model 200 with FBA metabolism 206, according to one embodiment. The full cell model 200 is an example of the modified FBA system 100 as shown in FIG. 1. Thus upstream sub-units 102 and downstream sub-units 114 may be any of the cellular repair sub-unit 202, the replication sub-unit 204, the gene expression sub-unit 208, and/or the cellular communication sub-unit 210. The arrows leading to the FBA metabolism 206 represent the input flux and/or output flux values between the FBA metabolism 206. Arrows between sub-units and FBA metabolism 206 may also represent the supply of molecules from these sub-units to FBA metabolism 206 and/or regulation of the sub-units on the FBA objective function.

As shown in FIG. 2, arrows lead from sub-units into FBA metabolism 206 and from FBA metabolism 206 into sub-units. This is an illustration of the fact that many cellular processes contain molecules and reaction pathways that are both inputs into FBA metabolism 206 and which are produced by FBA metabolism. Thus the sub-units shown in FIG. 2 may be both upstream sub-units and downstream sub-units, as described with reference to FIG. 1. The interactions between sub-units and FBA metabolism 206 may be coordinated by a single dataset that aggregates changes within the full cell model 200, such that each of the sub-units and FBA metabolism 206 receive and transmit information to the single dataset, rather than to each other. This single dataset may be a state dataset, and is described in further detail with reference to FIG. 3.

A. Molecule Cushions

In addition to molecule concentrations within sub-units and FBA metabolism 206, the full cell model 200 may include molecule cushions 212 that supplement molecule concentrations resulting from a system of supply and demand between the sub-units and FBA metabolism 206. The molecule cushions 212 represent reserves of molecules within the cellular environment. For example, molecule cushions 212 may be molecules that exist within a cell's cytoplasm, and which are available to molecular processes when needed. Molecule cushions 212 contain different reserve concentrations of different molecules. For example, a first molecule, $molecule_1$, may have a concentration $molecule_1$ concentration 214. If $molecule_1$ is a molecule that has a large flux value or demand within the system of sub-units and FBA metabolism 206, then the reserve concentration of $molecule_1$ may be larger than other molecules with smaller demand. Thus the concentration of molecules within molecule cushions 212 may be proportional to the flux value associated with the molecule in FBA metabolism, the aggregate demand for the molecule within the sub-units, and/or any other measurement of demand within the system of sub-units and FBA metabolism 206. The molecule cushions 212 ensure that sudden increases in demand for a molecule within the full cell model 200 do not result in complete depletions of a molecule within the full cell model 200.

There may be any number of molecules within molecule cushions 212. A total of N molecules, represented by $moleculeN$ concentration 214, are assigned reserve concentrations within molecule cushions 212. In some examples, all molecules within the full cell model 200 are assigned reserve concentrations within molecule cushions 212. In other examples, molecules with demand and/or flux values above a threshold are assigned reserve concentrations within molecule cushions 212, such that a subset of the molecules within the full cell model 200 representing the primary flow of molecules are stored in molecule concentrations $molecule_1$ concentration 214 through $moleculeN$ concentration 214.

The reserve concentrations of any of the molecules within the molecule cushions 212 are available for access by any sub-unit or other component of the full cell model 200 through a state dataset, which includes molecule concentration datasets 306 and 336, as described in further detail with reference to FIG. 3.

The effect of the molecule cushions 212 on the full cell model 200 is that the molecule cushion concentrations allow the demand for a molecule to instantaneously (e.g., for a given single time step evaluating the subunits) exceed supply without disrupting the full cell model 200. This allows the production network to continue to function as a demand load is applied to the system of the full cell model 200, giving the cell time to increase production of the molecule to meet the new demand. This process is illustrated with respect to FIG. 4.

IV. Modified FBA Time Series

Figure 3:
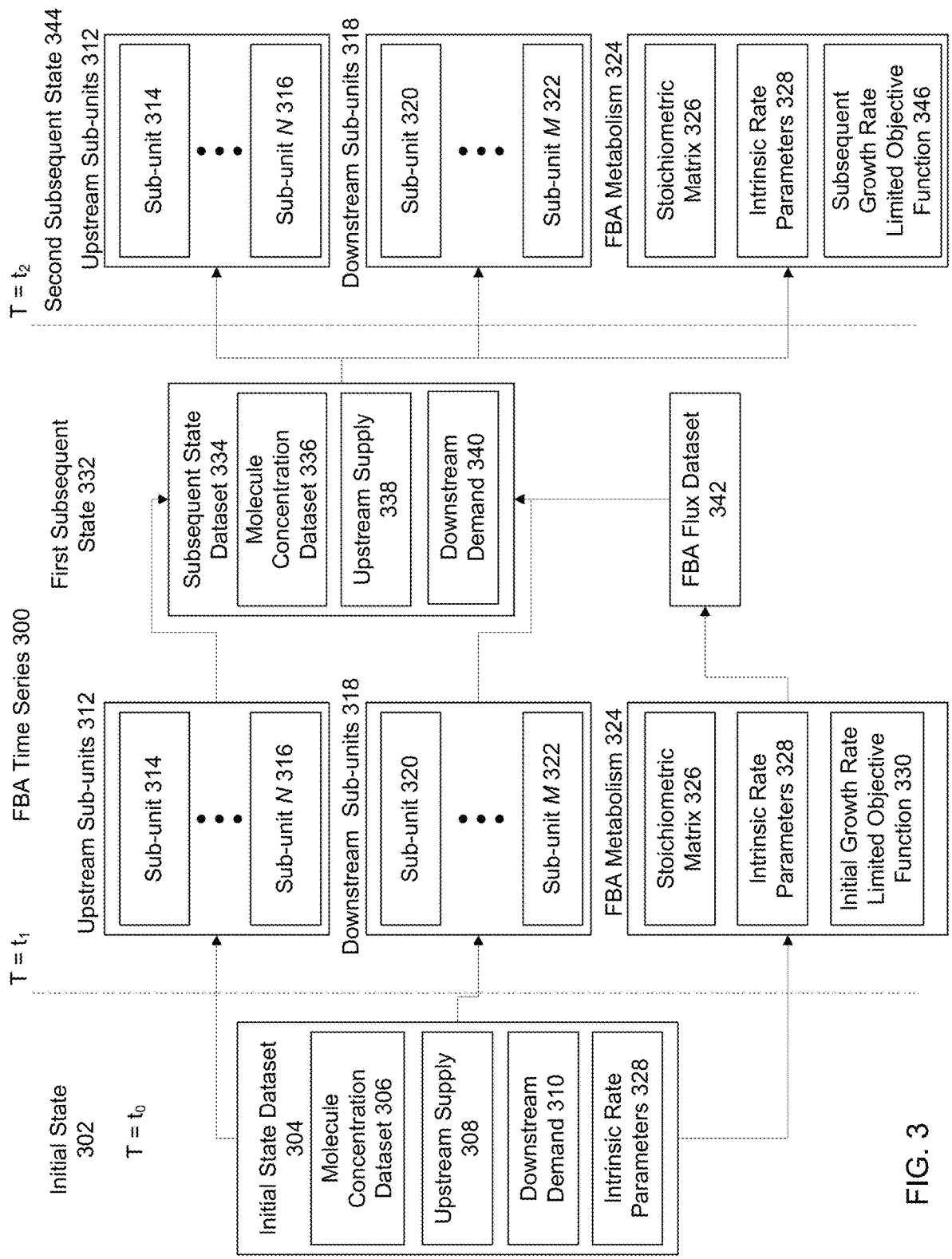
FIG. 3 is a block diagram of a time series using modified FBA metabolism, according to one embodiment.

FIG. 3 is a block diagram of a time series using FBA metabolism, according to one embodiment. An initial state 302 is established at $T=t_0$. Following the initial state 302, a first subsequent state 332 is determined by inputting the initial state dataset 304 into upstream sub-units 312, downstream sub-units 318 and FBA metabolism 324. The FBA metabolism 324 produces a set of solution flux values, which are output from FBA metabolism as FBA flux dataset 342. The FBA flux dataset 342 is combined with solutions to upstream sub-units 312 and downstream sub-units 318 to produce the subsequent state dataset 334. The subsequent state dataset 334 is an update of the initial state dataset 304. This subsequent state dataset 334 is a representation of the conditions in an FBA system at a first time step, $T=t_1$. The subsequent state dataset 334 is input into the upstream sub-units 346, downstream sub-units 352 and FBA metabolism 358 to produce the next time step at $T=t_2$.

A. Initial State Dataset

The initial state dataset 304 contains the molecule concentration dataset 306, the upstream supply 308 and downstream demand 310. Upstream supply 308 and downstream demand 310 are measured relative to the position of FBA metabolism within the production network spanning a full cell system, such as the modified FBA system 100 and/or the full cell model 200. Thus "upstream" refers to all sub-units and reaction pathways within sub-units that produce products that are used as inputs to FBA metabolism 324. "Downstream" refers to all sub-units and reaction pathways within sub-units that use the products of FBA metabolism 324 as input reactants. In some examples, sub-units and reaction pathways within sub-units may contain molecules that are both used as inputs to FBA metabolism 324 and that are products of FBA metabolism 324 and used as input reactants by the sub-unit. "Supply" and "Demand" refer to a rate of change of molecule concentrations within the upstream and downstream sub-units, respectively. For sub-units that contain differentiable functions describing molecular quantities, supply or demand may refer to the differential rate of change of the amount of a molecule within the sub-unit. For sub-units based on statistical or numerical approximations for the behavior of molecules within the sub-unit, "supply" and "demand" may refer to numerical approximations or inferred rates of change of the amount of a molecule within the sub-unit. Within the initial state dataset 304, these values are initialized for each molecule within FBA metabolism 324, upstream sub-units 312 and downstream sub-units 318 to simulate the starting conditions of the production network.

The initial state dataset 304 also includes molecule concentration dataset 306. The molecule concentration dataset 306 includes the initial concentrations of each molecule within each of the upstream sub-units 312, downstream sub-units 318, FBA metabolism, and the molecule cushion concentrations, such as the molecule cushions 212 as described with reference to FIG. 2. Thus the molecule concentration dataset 306 of the initial state dataset 304 sets the initial concentrations of the molecule cushions 212, as well as the initial concentrations within each of the upstream sub-units 312 and downstream sub-units 318. The molecule concentration dataset 306 represents the initialized "integral" amount of each molecule, such that the initial concentration dataset 306 constructs an artificial "history" for the cell model, representing previous behavior, growth, production, etc. that "occurred" before $T=t_0$. These initialized values may be adjusted to simulate cell growth and behavior within different mediums and extra-cellular environments.

The initial state dataset 304 also includes intrinsic rate parameters 328. The intrinsic rate parameters 328 are defined at the initial state 302 and are used as parameters within the FBA metabolism 324, and are discussed further below in connection to the FBA metabolism 324.

The initial state dataset 304 may additionally include any other data necessary to initialize the variables within the upstream sub-units 312, downstream sub-units 318 and FBA metabolism 324, including but not limited to boundary conditions, initial values other than molecule concentrations, and number of iterations for numerical simulations.

The initial state dataset 304 and any subsequent state datasets, such as subsequent state dataset 334, effectively coordinate supply and demand within the production network of FBA metabolism 324, upstream sub-units 312 and downstream sub-units 318. Thus upstream sub-units 312, downstream sub-units 318 and FBA metabolism 324 need not be linked together, and can instead interact through state datasets. Thus any change in the production network produced by any of the upstream sub-units 312 or downstream sub-units 318 is conveyed to the FBA metabolism 324 through an update in the state dataset. Similarly, any change in the production network produced by FBA metabolism 324 is conveyed to upstream and downstream sub-units 312 and 318 through an update in the state dataset.

B. First Time Step

The initial state dataset 304 is input into the upstream sub-units 312, downstream sub-units 318 and FBA metabolism 324, thus initializing the modified FBA system, such as modified FBA system 100 and/or the full cell model 200. Given the information within the initial state dataset 304, the systems represented within each upstream sub-unit, such as sub-unit 314 through sub-unit N 316, and each downstream sub-unit, such as sub-unit 320 through sub-unit M 322, can be fully simulated, producing a set of solutions that represent a subsequent state of each element within the sub-units given the initial conditions defined within the initial state dataset 304.

A subset of the upstream sub-units 312 and/or the downstream sub-units 318 may be time-dependent. Solutions to these sub-units are determined at the first subsequent state 332 for the time interval $t_1-t_0$. A remaining subset of the upstream sub-units 312 and downstream sub-units 318 are time-independent. For these sub-units, time independent solutions are found using the initial conditions within the initial state dataset 304 at the initial state 302 for $T=t_0$. Thus the time interval represented within the FBA time series 300 as $t_1-t_0$ between the first subsequent state 332 and the initial state 302 is interpreted to mean the time-independent solutions to the initial conditions at $T=t_0$. This is also the case for FBA metabolism 324.

IB. Time in FBA Metabolism

While an FBA formulation of metabolism is time independent, there is an implicit "time" variable built into an FBA model. This "time" is implicit in the steady-state assumption of FBA, meaning that the flux value FBA solutions are assumed to correspond to an undefined time at which intermediate fluctuations of flux values for each molecule have ended, and the entire system has reached a steady state. Steady state assumptions are often assumed to occur at $t \to \infty$ of the time dependent function. However, in order to use an FBA formulation of metabolism within a time series, one can adjust the steady state assumption to assume that the flux value solutions occur not at $t \to \infty$, but rather that the FBA metabolism 324 can achieve a steady state within the time interval $t_1-t_0$. To model the time interval between time steps from to to ti, the molecule concentration dataset 306, upstream supply 308, downstream demand 310 and intrinsic rate parameters 328 are input into FBA metabolism 324 as initial conditions. The resulting flux value solutions are thus the result of the FBA metabolism 324 reaching a steady state equilibrium as a result of these inputs, which can be interpreted as the FBA metabolism 324 reaching a steady state in the time interval $t_1-t_0$.

This same assumption can be used for other time-independent sub-units, such that the initial conditions for $T=t_0$ are input into time independent mathematical models, and the resulting solutions are interpreted to correspond to $T=t_1$ at which the system of production and consumption of molecules within the sub-unit has reached a steady state given the conditions at $T=t_0$.

IIB. Growth Rate Limited Objective Function

To construct a growth rate limited objective function, FBA begins with a reconstruction of a metabolic network describing the relationship between each product and reactant within metabolism (not shown). This network reconstruction includes every molecule and process of metabolism, however not all molecules and reactants of metabolism may be used to solve FBA metabolism 324 and/or the initial growth rate limited objective function 330. The metabolic network reconstruction is then converted into a stoichiometric matrix 326. The stoichiometric matrix 326 is a matrix of the stoichiometric coefficients of each reaction between molecules in the reaction pathways of metabolism. These stoichiometric coefficients are fixed by elemental and charge balance, and are time independent and do not change between iterative solutions to FBA metabolism. The stoichiometric matrix 326 serves as one set of reaction constraints on the production of FBA metabolism. The columns of the stoichiometric reaction matrix represent each of the j reactions within metabolism, while the rows represent each of the i molecules within metabolism. Each entry of the stoichiometric matrix is thus the stoichiometric coefficient of an ith molecule in the jth reaction of metabolism. An example of a stoichiometric matrix is shown below:

$$\begin{bmatrix} c_{11} & \cdots & c_{1j} \\ \vdots & \ddots & \vdots \\ c_{i1} & \cdots & c_{ij} \end{bmatrix} \quad (1)$$

Within each of the j reactions, molecules have a "flux value" meaning the net movement of the molecule through the "surface" of the reaction. A set of linear equations is written assuming mass balance of each molecule within the FBA metabolism 324, and resulting from the matrix equation:

$$\begin{bmatrix} c_{11} & \cdots & c_{1j} \\ \vdots & \ddots & \vdots \\ c_{i1} & \cdots & c_{ij} \end{bmatrix} * \begin{bmatrix} v_1 \\ \vdots \\ v_j \end{bmatrix} = 0 \quad (2)$$

Where each of the variables $v_1$ through $v_j$ are the unknown flux values for each of the j molecules. An example set of linear equations is given below that result from the above matrix multiplication:

$$c_{11}v_1 + c_{12}v_2 + \cdots = 0 \quad (3)$$
$$c_{21}v_1 + c_{22}v_2 + \cdots = 0$$
$$\vdots$$

In conventional FBA metabolism, these equations would be summed together to produce objective function:

$$\mathbb{Z} = \Sigma_{i=1}{}^i k_i v_i \quad (4)$$

However, as discussed previously, this objective function has a number of limitations and doesn't reflect supply and demand within the upstream sub-units 312 and downstream sub-units 318. Thus in addition to the summation above, the initial growth rate limited objective function 330 includes a set of target values for each molecule within FBA metabolism 324. The target values incorporate the intrinsic rate parameters 328, the upstream supply 308, the downstream demand 310 and the molecule concentration dataset 306 into a measurement of the target concentration of the molecule given supply, demand, and "on-hand" concentration of each molecule. The target values may be positive or negative. For purposes of unit conversion, so that target values can be included in the objective function and compared to the flux values, the target values are given as rates.

Target values are defined in part by a "net" demand measured within all sub-units of the overall production network in which FBA metabolism operates, such as modified FBA system 100 and/or full cell model 200. The net demand at the first subsequent state 332 is the difference between the downstream demand 310 and the upstream supply 308. In subsequent iterations and time steps, the net demand will be the difference between the downstream demand and the upstream supply of subsequent state datasets, such as the upstream supply 338 and downstream demand 340 of the subsequent state dataset 334.

In addition, the target values may be defined in part by an "amount on-hand" which represents the concentration of a molecule immediately available to a reaction pathway within FBA metabolism 324. In some examples, this is the concentration for each molecule present within the production network of FBA metabolism and upstream and downstream sub-units, as defined by the molecule concentration dataset 306. In other examples, this is the difference between the molecule concentration within the molecule concentration dataset 306 and the cushion concentration, such as molecule$_1$ concentration 214, within molecule cushions 212 as described in further detail with reference to FIG. 2. To convert the "amount on-hand" to a rate, these values are divided by a time interval.

The target values are further defined by a set of intrinsic rate parameters 328. The intrinsic rate parameters 328 represent the biological limits on metabolic production. For example, a cell may not be able to instantaneously increase its rate of production to meet downstream demand due to inherent rates of cellular processes, transportation of molecules, an enzyme or facilitating molecule$_1$s limited binding rate, or any other biological rate limit that is independent of molecular concentrations. Intrinsic rate parameters 328 represent further, inherent constraints on the production of metabolism in addition to the stoichiometric reaction constraints represented by the stoichiometric matrix 326. Intrinsic rate parameters 328 are a set of time independent coefficients. As described below, intrinsic rate parameters 328 limit the "derivative" response of production, the "integral" response of production, and the "second derivative" response of production of FBA metabolism to outside demand. Other intrinsic rate parameters 328 may limit a "proportional" response of production, or any higher order derivative responses of production.

For example, an intrinsic rate parameter is "inertia" which represents an intrinsic rate at which FBA metabolism 324 can supply a molecule to a reaction. "Inertia" is a "second derivative" limit of metabolic production within FBA metabolism 324, since it represents a limit on the instantaneous, "current" rate of change of production within FBA metabolism 324 and thus limits the rate at which the rate of change can itself adjust. "Inertia" has a damping effect on the rate at which a cell is able to produce the outputs of metabolism.

A second intrinsic rate parameter is "replenishment" which represents an intrinsic rate at which FBA metabolism can generate supply of a molecule to meet outside demand. "Replenishment" is a form of derivative control, in that it acts on the difference between an outside rate of demand and an internal rate of consumption of a molecule. Replenishment functions as a check on upstream supply sensitivity to downstream demand.

A third example of an intrinsic rate parameter is "half-life" of a molecule, which represents an intrinsic rate of consumption of a molecule within FBA metabolism. "Half-life" is an "integral" limit of metabolic production, since it represents previous production of a molecule within FBA metabolism.

Intrinsic rate parameters may be defined for each molecule within FBA metabolism, such that each molecule has its own "inertia," "replenishment," and "half-life" or any other defined intrinsic parameter rates that reflect the biological limitations of using the molecule as a reactant in a chemical reaction of metabolism. In some examples, different intrinsic rate parameters applied to the same molecules may be used for different sub-units, and a different set of intrinsic rate parameters may be used for FBA metabolism 324 than the upstream sub-units 312 and/or downstream sub-units 318. In some examples, the same set of intrinsic rate parameters is used for the same molecules in FBA metabolism 324, upstream sub-units 312 and downstream sub-units 318. In this example, the intrinsic rate parameters 328 are "global variables" and apply to molecules across all sub-units and FBA metabolism 324. The intrinsic rate parameters are used to determine the target values with which to modify the objective function at Equation 4 and produce the initial growth rate limited objective function 330. An example of the way intrinsic rate parameters 328 affect the response of metabolic production of FBA metabolism 324 to demand within upstream and downstream sub-units 312 and 318, respectively, is described in further detail with reference to FIG. 4.

For each molecule in FBA metabolism 324, a target value is calculated and incorporated into the objective function at Equation 4 to produce the initial growth rate limited objective function 330. This may be in the form of calculating an absolute difference between the target value and the proportional flux contribution of each molecule. This may be in the form of scaling the proportional flux contribution of each molecule. This may be in the form of adding to the proportional flux contribution of each molecule. Any other mathematical modification of the proportional flux contribution of each molecule that adjusts this value by the target value may be used. As an example, the initial growth rate limited objective function 330 may be in the form:

$$\mathbb{Z} = \Sigma_{i=1}{}^j |k_i v_i - \text{target}_i| \quad (5)$$

where $target_i$ is the target value for each ith molecule and the proportional flux contribution term $k_i v_i$ is modified by finding an absolute value difference between it and the calculated target value. The target value modification of the proportional flux contribution of each molecule may be the downstream regulation 120 of downstream sub-units 114 on FBA metabolism 110 as described in further detail with reference to FIG. 1.

The initial growth rate limited objective function 330 is calculated based on the initial state dataset 304 provided at initial state 302. The initial growth rate limited objective function 330 is subsequently solved for each flux value $v_i$ for the molecules within FBA metabolism 324. In some examples, the number of flux values $v_i$ may be less than the total number of molecules within the reconstructed metabolic network of FBA metabolism 324. The solutions to FBA metabolism 324 make up the FBA flux dataset 342. FBA flux dataset 342 may include the input flux dataset 108 and output flux dataset 112 as described in further detail with reference to FIG. 1.

IVB. Upstream and Downstream Sub-Units

The initial state dataset 304 contains the initial conditions for each of the N upstream sub-units 312 and each of the M downstream sub-units 318. Using these initial conditions from the initial state 302 at $T=t_0$, the solutions to each of the N upstream sub-units 312 and each of the M downstream sub-units 318 are solved at the first subsequent state 332 for $T=t_1$. Solving the upstream sub-units 312 and downstream sub-units 318 may entail running a Monte Carlo simulation, solving a system of ODEs, PDEs, using iterative numerical methods, or any other form of deriving mathematical solutions for multi-variable systems. The solutions to the upstream sub-units 312 and downstream sub-units 318 are included in the subsequent state dataset 334.

Following solving the upstream sub-units 312 and downstream sub-units 318, the subsequent state dataset 334 is determined. Molecule concentration dataset 336 is updated from the initial state dataset 304 to include the molecule concentrations present within the upstream sub-units 312, downstream sub-units 318, and FBA metabolism 324 at the first subsequent state 332. Additionally, upstream supply 338 and downstream demand 340 are calculated from the solutions to the upstream sub-units 312 and downstream sub-units 318. Within each of the upstream sub-units 312 and downstream sub-units 318, there is an instantaneous or approximate rate of change for each molecule within the sub-units. This rate of change may be a differential value, or may be a numerical approximation. These instantaneous or approximated rates of change are aggregated for each molecule within FBA metabolism to produce a measurement of upstream supply 308 and downstream demand 310. Thus for each molecule within FBA metabolism, there may be an upstream supply 338 value derived from the solutions to the upstream sub-units 312, and a downstream demand 340 value derived from the solutions to the downstream sub-units 318.

The subsequent state dataset 334 thus replaces the initial state dataset 304 as the full descriptor of "conditions" within a production network with FBA metabolism. Subsequent state dataset 334 is used as the initial condition for the next time step of the production network.

C. Second Time Step

In the second subsequent state 344, the same upstream sub-units 312, downstream sub-units 318, and FBA metabolism 324 are used as in the first subsequent state 332. The sub-units within the upstream sub-units 312 (sub-unit 314 through sub-unit N 316) are the same as in the first subsequent state 332, as are the sub-units within downstream sub-units 318 (sub-unit 320 through sub-unit M 322). The stoichiometric matrix 326 and intrinsic rate parameters 328 are the same as used in the first subsequent state 332. Thus all aspects of the sub-units and FBA metabolism 324 remain the same across successive time steps of the production network, except for an update to the growth rate limited objection function and the initial conditions used to find solutions to upstream sub-units 312, downstream sub-units 318, and FBA metabolism 324.

As previously described, the initial growth rate limited objective function 330 consists of a summation of the proportional flux value contributions of each molecule as modified by a set of target values. Using the subsequent state dataset 334 a new set of target values is calculated for every molecule within FBA metabolism 324. The initial growth rate limited objection function 330 is thus modified to produce the subsequent growth rate limited objective function 346. Thus between the time step $T=t_1$ and $T=t_2$, FBA metabolism 324 is modified to reflect the different conditions within the production network, as represented in the difference between the initial state dataset 304 and the subsequent state dataset 334.

The upstream sub-units 312, downstream sub-units 318, and FBA metabolism 324 are all solved with the initial conditions of the subsequent state dataset 334. The solutions produce a new set of molecule concentrations, upstream supply and downstream demand (not shown) which in turn produce a second subsequent state dataset 334 the reflects the new conditions within the production network at the second subsequent state 344.

D. Iterative Solutions to Produce Time Series

Thus at each time step in a time series, upstream sub-units 312, downstream sub-units 318 and FBA metabolism 324 are solved using the initial conditions provided in the state dataset of the previous time step. The objective function of FBA metabolism 324 is updated with new target values calculated from the state dataset of the previous time step. Solutions to the upstream sub-units 312, downstream sub-units 318 and FBA metabolism 324 are then used to update the state dataset of the previous time step and produce a new state dataset. This new state dataset is then used in the next iteration.

A growth rate of a cell or overall production rate of a production network (as represented by the upstream sub-units 312, downstream sub-units 318 and FBA metabolism 324) can be determined by calculating a difference between successive state datasets and dividing this difference by the time interval represented by these state datasets. For example, a growth rate of the FBA time series 300 as shown in FIG. 3 can be calculated from a difference between the first subsequent state 332 and the initial state 302 and dividing by the time interval $t_1 - t_0$. Additionally or alternatively, a growth rate of a cell can be determined by calculating a difference between the objective functions and flux value solutions to FBA metabolism 324. As previously mentioned, the growth rate limited objective function of FBA metabolism 324 represents a total biomass of a cell, and thus calculating the difference between objective functions may represent a difference in total cell growth over a time interval within the time series.

The FBA time series 300 may be iteratively solved until the difference in growth rates between subsequent time steps reaches a threshold value. This threshold value may represent homeostasis of the production network given the initial conditions described at the initial state 302. Thus as the difference between growth rates becomes smaller, this may indicate that the production network has reached a steady state, the FBA time series 300 may end.

Thus through iterative solutions to FBA metabolism 324 within a larger production network, the input and output flux values of FBA metabolism 324 can be regulated such that they meet downstream demand given upstream supply.

V. Outcome of a Cell Process

An outcome of a cell process can be determined using the iterative solutions of the FBA time series 300. An outcome of a cell process is any numerical solution to a network model of the cell process. Each sub-unit, groups of sub-units, and the full cell model encompassing all sub-units may each have an associated outcome. Each cell process may have multiple outcomes, where each outcome has a different unit of measure. For example, a first outcome may be a change in pH, while a second outcome may be the number of molecules of ATP produced (e.g., molecule count is measured). Each of these outcomes may be derived from the same numerical solution of the network model of the cell process, since the numerical solution can be converted into different metric units. An outcome of a cell process is calculated across a time interval, and thus represents a change in a cell process from a first state at a first time to a second state at a subsequent time. For models such as FBA that are time independent, the outcome of a cell process may be calculated between an initial state of initial conditions, and the time independent solution to the model. Thus the "initial conditions" are considered a first state, the numerical solutions a second state, and the "time interval" across the two states.

Each outcome of a cell process may be measured from the numerical solution of any individual sub-unit or from combining numerical solutions of groupings of sub-units within the full cell model 200. For example, the outcome of a cell process may be measured for a metabolism by calculating an outcome from the numerical solutions to FBA metabolism. The outcome of FBA metabolism 324 may be measured by calculating a difference between solution flux values calculated at different time steps, such as between the FBA flux dataset 324 and a subsequent flux dataset calculated from the subsequent growth rate limited objective function 346. While outcomes can be calculated across each sub-unit, the state datasets aggregate outcomes across all sub-units. Differences between state datasets are thus used to determine outcomes for the full cell model 200. For example, an outcome for a full cell model 200 may be determined by calculating a difference between the initial state dataset 304 and the subsequent state dataset 334. Examples of outcomes of cell processes are described in the following FIGS. 4-6.

VI. ATP Concentration Example

Figure 4:
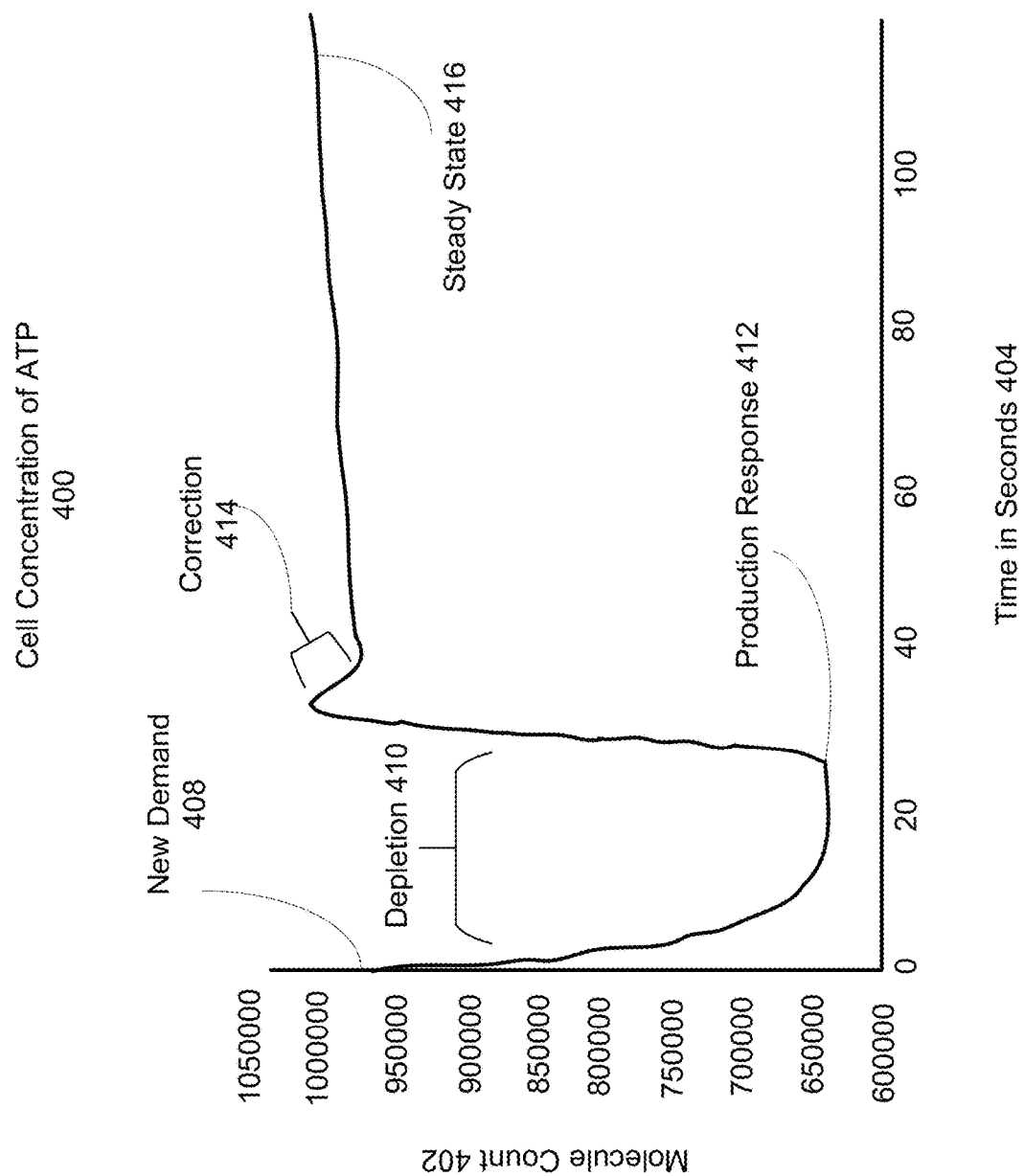
FIG. 4 is an example graph of the ATP concentration within a cell implementing a modified FBA system, according to one embodiment.

FIG. 4 is an example graph of the ATP concentration within a cell implementing a modified FBA system. The cell concentration of ATP 400 is an example of an outcome of a cell process. The cell concentration of ATP 400 reflects the concentration of ATP within FBA metabolism, upstream sub-units, downstream sub-units, and the cushion concentration of ATP, as shown with reference to FIGS. 1-3. The cell concentration of ATP 400 may be determined by calculating differences between state datasets, such as the initial state dataset 304 and subsequent state dataset 334. The behavior of the cell concentration of ATP 400 reflects the limits on metabolic production within FBA metabolism that the growth rate limited objective function imposes.

The x-axis reflects the molecule count 402 of ATP molecules within the production network. The y-axis gives the time in seconds 404. The cell concentration of ATP 400 reflects multiple iterative time step solutions to FBA metabolism, such as that described in the FBA time series 300 with reference to FIG. 3.

In the example shown, a new demand 408 is applied to the production network. The new demand may come from one or more downstream sub-units from FBA metabolism. In response to the new demand 408, the concentration of ATP within the cell is depleted at depletion 410. During depletion 410, the production of ATP within FBA metabolism may not have sufficiently increased to meet the downstream demand, so the overall concentration of ATP goes down. The production of ATP within FBA metabolism may have a time lag in response to the downstream demand before production rates are able to match the downstream demand. However, this initial depletion 410 reflects the biological limits of metabolism, and may therefore be an accurate simulation of a cell's response to new demand 408. Cushion concentrations of ATP may prevent the depletion 410 from resulting in zero or "negative" concentrations of ATP within the production network.

After successive iterations of solving FBA metabolism in the time series represented in FIG. 4, the growth rate limited objective function of FBA is updated to reflect the new downstream demand of new demand 408, until FBA production reaches the production response 412. After this time step, the production of ATP within FBA metabolism increases, and the concentration of ATP within the cell rises to meet the downstream demand. As shown at correction 414, it is possible that the production response of FBA metabolism may over-correct production in response to the new demand 408. However, in successive iterative solutions to FBA metabolism, the spike in production is reduced to reflect the fact that the concentration of ATP matches the downstream demand. At correction 414, the production rate of ATP within FBA metabolism is reduced to meet the new demand 408. The production of ATP then reaches a steady state 416, at which point the cell has returned to homeostasis following the new demand 408.

The time lag between new demand 408 and production response 412, as well as the curve slopes shown in FIG. 4 may be defined by the intrinsic rate parameters 328 as described with reference to FIG. 3. For example, the proportional parameter (e.g., replenishment) may determine the duration of the time lag between new demand 408 and production response 412, while the derivative parameter (e.g., inertia) defines the slope of the response curve between production response 412 and correction 414, while the integral parameter (e.g., half-life) defines the depletion rate 410.

The cell concentration of ATP 400 demonstrates the modified FBA metabolism's ability to alter production to match downstream demand.

VII. Macromolecule Concentrations Example

Figure 5:
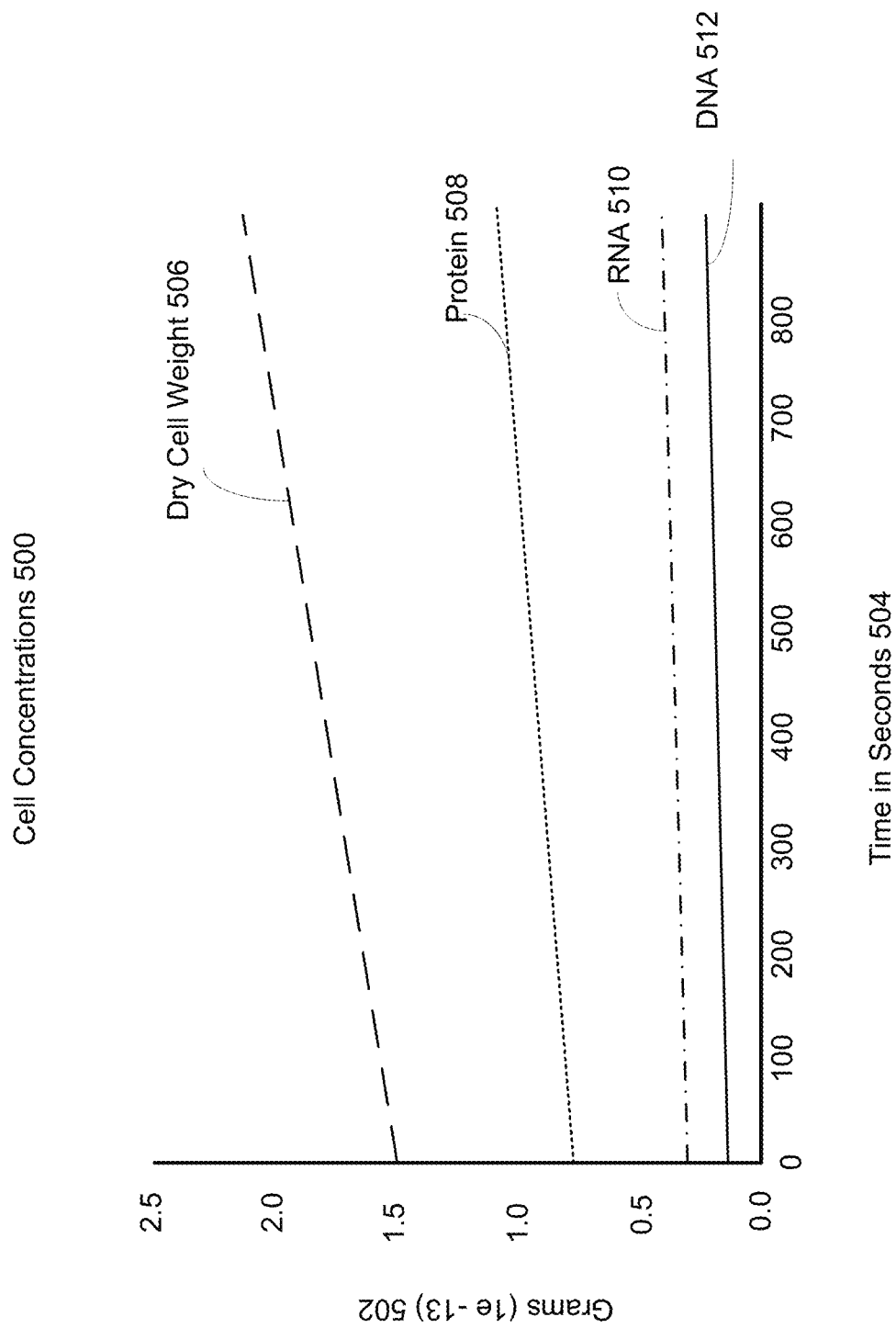
FIG. 5 is an example graph of several molecule concentrations within a cell implementing a modified FBA system, according to one embodiment.

FIG. 5 is an example graph of several molecule concentrations within a cell implementing a modified FBA system. Cell concentrations 500 of various macromolecules are shown, and reflect the given macromolecule concentrations across FBA, upstream sub-units, downstream sub-units, and cushion concentrations. The cell concentrations 500 are examples of outcomes of a cell process, and may be calculated from differences between state datasets. The change in cell concentrations 500 over time is determined through iterative solutions to the modified FBA system, as shown with reference to FIG. 1-3. The x-axis gives the time in seconds 504, while the y-axis gives the macromolecule concentrations in grams (1e–13) 502.

The dry cell weight 506 gives the total biomass within a modified FBA system. In a pure FBA system, the dry cell weight 506 is synonymous with the objective function, however in a modified FBA system the dry cell weight 506 reflects the biomass within FBA metabolism, upstream and downstream sub-units, and the cushion concentrations. Individual macromolecules that contribute to the dry cell weight 506 are shown below, as protein 508, RNA 510 and DNA 512. A derivative of the dry cell weight 506 curve may be used as a cell growth rate. The dry cell weight 506 derivative may be compared to real-life expected call growth rates, primary literature, or any other reference materials to determine the accuracy of the modified FBA system. Derivatives of any of the macromolecules protein 508, RNA 510 and/or DNA 512 may similarly be determined as individual macromolecule rates and compared to real-life expected rates, primary literature, or any other reference materials to determine the accuracy of the modified FBA system.

VIII. Amino Acid Concentrations Example

Figure 6:
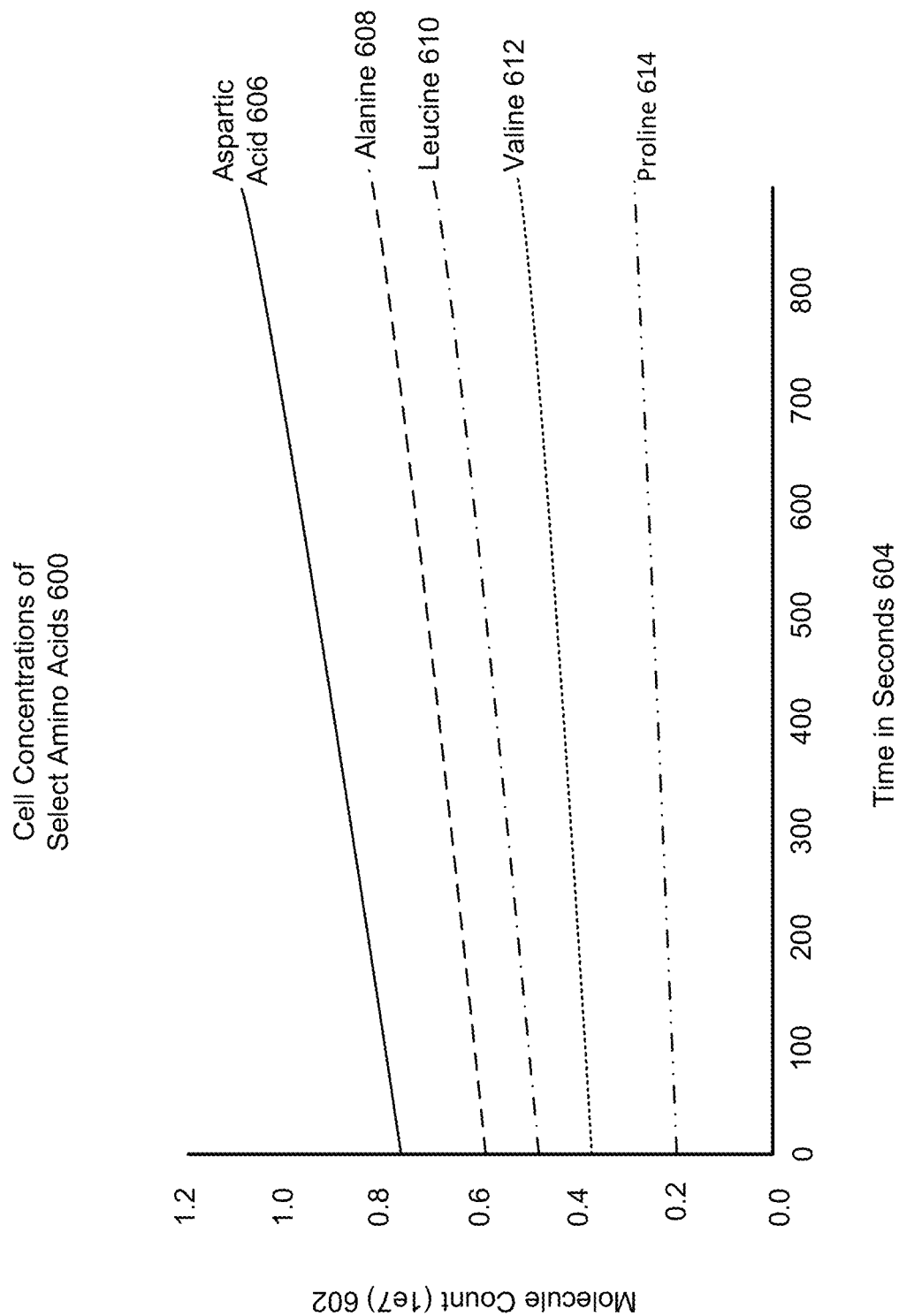
FIG. 6 is an example graph of amino acid concentrations within a cell implementing a modified FBA system, according to one embodiment.

FIG. 6 is an example graph of amino acid concentrations within a cell implementing a modified FBA system. The cell concentrations of select amino acids 600 reflect concentrations across FBA metabolism, upstream and downstream sub-units, and cushion concentrations, and are generated through iterative solutions to a modified FBA system. The cell concentrations of select amino acids 600 are examples of outcomes of a cell process, and may be calculated from a difference between state datasets. The x-axis gives time in seconds 604, while the y-axis gives the molecule count (1e7) 602. The concentration curves for aspartic acid 606, alanine 608, Leucine 610, valine 612 and proline 614 all reflect regulated production as determined by FBA metabolism. The growth rates of any of these curves may be compared to real-life growth expectancies, primary literature, or any other reference materials to determine the accuracy of the modified FBA system.

IX. Additional Considerations

A number of embodiments have been described. Nevertheless, it will be understood that various modifications may be made without departing from the spirit and scope of the invention.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for simulating an outcome of a cell process of at least one cell in a production network, the method comprising:

receiving an initial state dataset based on initial net demand for a plurality of molecules in a plurality of sub-units representing production and consumption of molecules external to a flux balance analysis (FBA) system, wherein multiple sub-units of the plurality of sub-units represent transcription, translation, cellular communication, cellular respiration, cellular reproduction, or cellular transport;

calculating an initial solution flux dataset by evaluating the FBA system based on a stoichiometric matrix and an objective function, the objective function based on a difference between a first target value for each molecule of the plurality of molecules and a first proportional flux contribution of each molecule of the plurality of molecules, wherein the first target value is included in a set of initial target values calculated based on the initial state dataset;
receiving a subsequent net demand for the plurality of molecules from initial solutions to the plurality of sub-units;
calculating a subsequent state dataset for the plurality of molecules in the plurality of sub-units based on the initial state dataset, the initial solution flux dataset, and the subsequent net demand;
updating the objective function, the updated objective function based on a difference between a second target value for each molecule of the plurality of molecules and a second proportional flux contribution of each molecule of the plurality of molecules, wherein the second target value is included in a set of subsequent target values calculated based on the subsequent state dataset;
calculating a subsequent solution flux dataset by evaluating the FBA system with the updated objective function; and
determining the outcome of the cell process of the at least one cell, the determining includes calculating a difference between the subsequent solution flux dataset and the initial solution flux dataset, wherein the outcome of the cell process corresponds to an estimation of a growth rate of the at least one cell, and wherein an accuracy of the updated objective function is determined based on a comparison of the estimation of the growth rate of the at least one cell to an actual growth rate of the at least one cell.

2. The method of claim 1, wherein:
the initial state dataset includes a set of initial molecule concentrations of the plurality of molecules; and
the initial net demand for the plurality of molecules comprises:
an initial rate of supply in a first sub-unit representing production upstream from metabolism; and
an initial rate of demand in a second sub-unit representing consumption downstream from metabolism.

3. The method of claim 2, wherein the set of initial molecule concentrations of the plurality of molecules comprises:
a total concentration of each of the plurality of molecules in the plurality of sub-units; and
a cushion concentration representing a reserve concentration of each of the plurality of molecules.

4. The method of claim 1, wherein the initial state dataset further includes:
a set of intrinsic rate parameters for each of the plurality of molecules, wherein the set of intrinsic rate parameters represents a biological ability of the cell to adjust the subsequent solution flux dataset to the subsequent net demand for the plurality of molecules.

5. The method of claim 4, wherein the set of intrinsic rate parameters for each of the plurality of molecules includes at least one of: a proportional rate limit, an integral rate limit, and a derivative rate limit.

6. The method of claim 1, wherein calculating the initial solution flux dataset by evaluating the FBA system based on the stoichiometric matrix and the objective function limited by the initial state dataset further comprises:
maximizing the objective function limited by the initial state dataset within a constraint of the stoichiometric matrix to determine a maximum growth rate.

7. The method of claim 1, wherein the initial solution flux dataset comprises:
a set of input fluxes representing in part an initial rate of supply in a first set of sub-units representing production and consumption upstream from metabolism; and
a set of output fluxes representing in part an initial rate of demand in a second set of sub-units representing production and consumption downstream from metabolism.

8. The method of claim 1, wherein the initial net demand for the plurality of molecules in the plurality of sub-units representing production and consumption of molecules external to the FBA system is determined by at least one of: a Monte Carlo method, solving a set of ordinary differential equations (ODEs), and solving a set of partial differential equations (PDEs).

9. The method of claim 1, wherein:
the initial state dataset is associated with a first time;
the subsequent state dataset is associated with a subsequent time; and
the difference between the subsequent solution flux dataset and the initial solution flux dataset represents metabolic production over a time interval between the first time and the subsequent time.

10. The method of claim 1, further comprising:
calculating the subsequent solution flux dataset by evaluating the FBA system with the updated objective function limited by the subsequent state dataset until a change in a growth rate of the cell reaches a threshold.

11. The method of claim 10, wherein the threshold is associated with homeostasis of the cell.

12. A non-transitory computer readable storage medium containing computer program code executable on a processor for causing the processor to perform operations for simulating an outcome of a cell process of at least one cell in a production network, the operations comprising:
receiving an initial state dataset based on initial net demand for a plurality of molecules in a plurality of sub-units representing production and consumption of molecules external to a flux balance analysis (FBA) system, wherein multiple sub-units of the plurality of sub-units represent transcription, translation, cellular communication, cellular respiration, cellular reproduction, or cellular transport;
calculating an initial solution flux dataset by evaluating the FBA system based on a stoichiometric matrix and an objective function, the objective function based on a difference between a first target value for each molecule of the plurality of molecules and a first proportional flux contribution of each molecule of the plurality of molecules, wherein the first target value is included in a set of initial target values calculated based on the initial state dataset;
receiving a subsequent net demand for the plurality of molecules from initial solutions to the plurality of sub-units;
calculating a subsequent state dataset for the plurality of molecules in the plurality of sub- units based on the initial state dataset, the initial solution flux dataset and the subsequent net demand;
updating the objective function, the updated objective function based on a difference between a second target value for each molecule of the plurality of molecules and a second proportional flux contribution of each molecule of the plurality of molecules, wherein the second target value is included in a set of subsequent target values calculated based on the subsequent state dataset;

calculating a subsequent solution flux dataset by evaluating the FBA system with the updated objective function; and determining the outcome of the cell process of the at least one cell, the determining includes calculating a difference between the subsequent solution flux dataset and the initial solution flux dataset, wherein the outcome of the cell process corresponds to an estimation of a growth rate of the at least one cell, and wherein an accuracy of the updated objective function is determined based on a comparison of the estimation of the growth rate of the at least one cell to an actual growth rate of the at least one cell.

13. The non-transitory computer readable storage medium of claim 12, wherein:

the initial state dataset includes a set of initial molecule concentrations of the plurality of molecules; and the initial net demand for the plurality of molecules comprises:

an initial rate of supply in a first sub-unit representing production upstream from metabolism; and an initial rate of demand in a second sub-unit representing consumption downstream from metabolism.

14. The non-transitory computer readable storage medium of claim 13, wherein the set of initial molecule concentrations of the plurality of molecules comprises:

a total concentration of each of the plurality of molecules in the plurality of sub-units; and a cushion concentration representing a reserve concentration of each of the plurality of molecules.

15. The non-transitory computer readable storage medium of claim 12, wherein the initial state dataset further includes:

a set of intrinsic rate parameters for each of the plurality of molecules, wherein the set of intrinsic rate parameters represents a biological ability of the cell to adjust the subsequent solution flux dataset to the subsequent net demand for the plurality of molecules.

16. The non-transitory computer readable storage medium of claim 15, wherein the set of intrinsic rate parameters for each of the plurality of molecules includes at least one of: a proportional rate limit, an integral rate limit, and a derivative rate limit.

17. The non-transitory computer readable storage medium of claim 12, wherein calculating the initial solution flux dataset by evaluating the FBA system based on the stoichiometric matrix and the objective function limited by the initial state dataset further comprises:

maximizing the objective function limited by the initial state dataset within a constraint of the stoichiometric matrix to determine a maximum growth rate.

18. The non-transitory computer readable storage medium of claim 12, wherein the initial solution flux dataset comprises:

a set of input fluxes representing in part an initial rate of supply in a first set of sub-units representing production and consumption upstream from metabolism; and a set of output fluxes representing in part an initial rate of demand in a second set of sub-units representing production and consumption downstream from metabolism.

19. The non-transitory computer readable storage medium of claim 12, wherein the initial net demand for the plurality of molecules in the plurality of sub-units representing production and consumption of molecules external to the FBA system is determined by at least one of: a Monte Carlo method, solving a set of ordinary differential equations (ODEs), and solving a set of partial differential equations (PDEs).

20. The non-transitory computer readable storage medium of claim 12, wherein:

the initial state dataset is associated with a first time;

the subsequent state dataset is associated with a subsequent time; and the difference between the subsequent solution flux dataset and the initial solution flux dataset represents metabolic production over a time interval between the first time and the subsequent time.

21. The non-transitory computer readable storage medium of claim 12, further comprising:

calculating the subsequent solution flux dataset by evaluating the FBA system with the updated objective function limited by the subsequent state dataset until a change in a growth rate of the cell reaches a threshold.

22. The non-transitory computer readable storage medium of claim 21, wherein the threshold is associated with homeostasis of the cell.

* * * * *